United States Patent [19]

Torigoe et al.

[11] Patent Number: 4,610,954
[45] Date of Patent: Sep. 9, 1986

[54] SILVER HALIDE PHOTOGRAPHIC LIGHT-SENSITIVE MATERIAL

[75] Inventors: Masaaki Torigoe; Yoshio Inagaki; Tadao Shishido, all of Kanagawa, Japan

[73] Assignee: Fuji Photo Film Co., Ltd., Kanagawa, Japan

[21] Appl. No.: 669,297

[22] Filed: Nov. 8, 1984

[30] Foreign Application Priority Data

Nov. 8, 1983 [JP] Japan ................. 58-209529
Nov. 8, 1983 [JP] Japan ................. 58-209530

[51] Int. Cl.⁴ ............................... G03C 1/34
[52] U.S. Cl. ......................... 430/445; 430/611; 430/533; 430/531; 430/538; 430/448
[58] Field of Search .......... 430/611, 600, 533, 531, 430/538, 445, 448

[56] References Cited

U.S. PATENT DOCUMENTS 3,433,640 3/1969 Nishio et al. ............ 430/600
3,723,125 3/1973 Hayashi et al. .......... 430/379
4,328,302 5/1982 Nishimura et al. ........ 430/611

FOREIGN PATENT DOCUMENTS 680889 2/1964 Canada ................. 430/611
57-14836 1/1982 Japan .................. 430/611
2080963 2/1982 United Kingdom ......... 430/611

Primary Examiner—Won H. Louie
Attorney, Agent, or Firm—Sughrue, Mion, Zinn, Macpeak, and Seas

[57] ABSTRACT

A silver halide photographic light-sensitive material for obtaining a silver image comprising a water-impermeable support having at least one silver halide emulsion layer, and containing in association with the emulsion layer a compound selected from the group consisting of: (a) a compound represented by the following general formula (I):

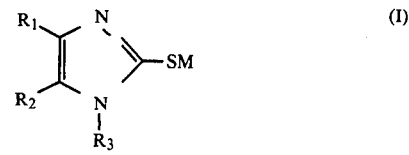

(b) a compound represented by the following general formula (II):

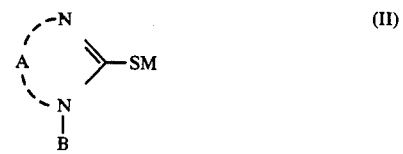

and (c) a combination of a compound represented by the following general formula (III) and a compound represented by the following general formula (IV):

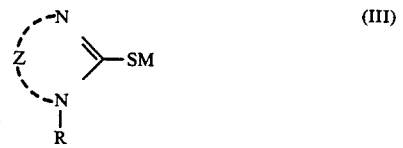

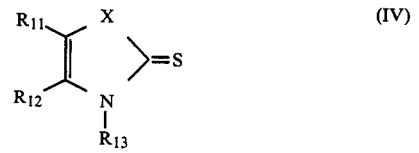

(all the symbols are as defined in the appended claims), and a method of forming silver images using the above-defined silver halide photographic light-sensitive material, are disclosed.

23 Claims, No Drawings

SILVER HALIDE PHOTOGRAPHIC LIGHT-SENSITIVE MATERIAL

FIELD OF THE INVENTION

This invention relates to a silver halide photographic light-sensitive material for obtaining a silver image and more particularly, to a silver halide photographic light-sensitive material having a water-impermeable support with reduced deterioration of the silver image with time.

BACKGROUND OF THE INVENTION

In the field of silver halide photographic light-sensitive materials, due to their greater fastness silver images are better suited for recording information required to be permanent than color images (dye images). However, even silver images tend to deteriorate with time. This tendency is aggravated when water-impermeable supports such as plastic films are used as supports. Water-impermeable supports such as platic films are generally better suited for long periods of storage due to their strength, which is higher than that of water-permeable supports such as paper or cloth but, on the other hand, they increase silver image deterioration as described above. Deterioration of silver images on such water-impermeable supports has been reported in *Photographic Science and Engineering*, Vol. 7, pp. 253–261 (1963), British Patent Application (published unexamined) No. 2,019,024A.

Techniques for preventing deterioration of silver images are disclosed in Japanese Patent Application (OPI) No. 14836/82 (British Patent Application (published unexamined) No. 2,080,963A), which use mercaptobenzimidazole compounds and mercaptotetraazaindene compounds (the term "OPI" as used herein refers to a "published unexamined Japanese patent application").

However, the compounds described in the above-described Japanese patent application have the disadvantages that they seriously reduce the sensitivity of the photographic material or result in serious image-blackening by side exposure. The term "image-blackening by side exposure (after-exposure)" means that when light-sensitive materials, after imagewise exposure and before development processing, are exposed, for example, to light from a safelight transmitted through a faded filter (e.g., a filter having been used for one year or more), they are "after exposed" and the entire light-sensitive material appears somewhat blackish after beind developed. The finished images have decreased contrast and an inferior overall impression, and the photographic materials have greatly diminished value as photographic light-sensitive materials.

SUMMARY OF THE INVENTION

An object of the present invention is to prevent deterioration with time of silver images which occurs when water-impermeable supports are used.

Another object of the present invention is to provide a silver halide photographic light-sensitive material containing an anti-fogging agent which preserves sensitivity and which reduces image-blackening by side exposure.

A further object of the present invention is to provide a method of forming silver images free from deterioration with time and blackening by side exposure.

These and other objects of the present invention have been successfully attained by a silver halide photographic light-sensitive material comprising a water-impermeable support having at least one silver halide emulsion layer, and containing in association with the emulsion layer a compound selected from the group consisting of: (a) a compound represented by the following general formula (I):

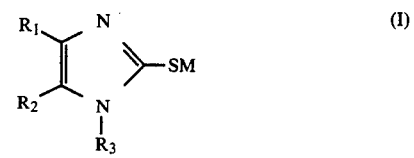

wherein $R_1$ and $R_2$, which may be the same or different, each represents a hydrogen atom, an alkyl group, an aryl group, or a hetero ring group, $R_3$ represents a phenyl group having at least one carboxyl group, and M represents a hydrogen atom, $NH_4$ or an alkali metal atom; (b) a compound represented by the following general formula (II):

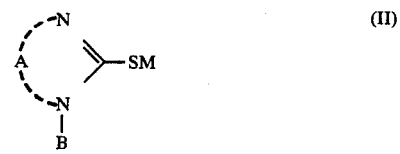

wherein A represents an atomic group necessary for forming a hetero ring, including a 5- to 7-membered ring, B represents an alkyl, aryl or hetero ring group each substituted with at least one sulfo group, and M represents a hydrogen atom, $NH_4$ or an alkali metal atom; and (c) a combination of a compound represented by the following general formula (III) and a compound represented by the following general formula (IV):

wherein M represents a hydrogen atom, $NH_4$ or an alkali metal atom, R represents a hydrogen atom, an alkyl group or an aryl group, and Z represents an atomic group necessary for forming a 5-membered hetero ring or an atomic group necessary for forming a 5-membered hetero ring fused with a benzene ring; and

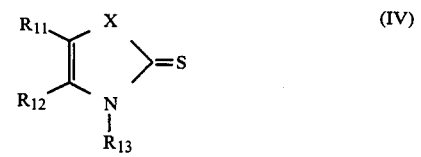

wherein X is selected from the group consisting of a sulfur atom, an oxygen atom, a selenium atom, $>N-R_{14}$, wherein $R_{14}$ represents an alkyl group, an aralkyl group or an aryl group, and $-CH=CH-$, $R_{11}$ and $R_{12}$, which may be the same or different, each represents a hydrogen atom, an alkyl group, an aryl group or an alkoxycarbonyl group, provided that $R_{11}$ and $R_{12}$ may combine to form a 5- or 6-membered ring, and $R_{13}$ represents an alkyl group, an aralkyl group or an aryl group.

DETAILED DESCRIPTION OF THE INVENTION

In general formula (I), the alkyl group represented by $R_1$ or $R_2$ may be substituted by a halogen atom (e.g., a chlorine atom or a bromine atom), an alkoxy group, a hydroxyl group, and includes a methyl group, an ethyl group, a methoxyethyl group, an ethoxyethyl group, a chloroethyl group, and a benzyl group, with groups containing 1 to 14 carbon atoms being preferred.

The aryl group represented by $R_1$ or $R_2$ may be substituted by a halogen atom (e.g., a chlorine atom or a bromine atom), an alkyl group, an alkoxy group, an alkylsulfonyl group, an arylsulfonyl group, a sulfamoyl group, an alkylsulfonamido group, an arylsulfonamido group, a carbamoyl group or a carbonamido group, with groups containing 6 to 14 carbon atoms being preferred.

As the hetero ring group represented by $R_1$ or $R_2$, substituted or unsubstituted, 5- or 7-membered rings containing one or more of at least one kind of nitrogen, oxygen, and sulfur are preferred.

The number of carboxyl groups in the phenyl group represented by $R_3$ is preferably 1 or 2.

The phenyl group represented by $R_3$ may further be substituted by a halogen atom (e.g., a chlorine atom or a bromine atom), an alkyl group (e.g., a methyl group or an ethyl group), an alkoxy group (e.g., a methoxy group or an ethoxy group), an alkylsulfonyl group, an arylsulfonyl group, a sulfamoyl group, an alkylsulfonamido group, an arylsulfonamido group, a carbamoyl group or a carbonamido group. These substituents preferably contain up to 14 carbon atoms.

Of the compounds represented by general formula (I), preferred examples are illustrated below. However, the scope of the present invention is not to be construed as being limited thereto.

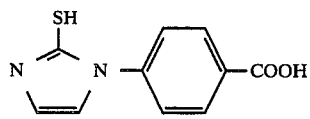

I-1

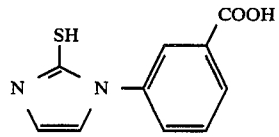

I-2

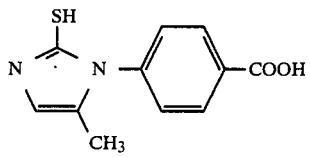

I-3

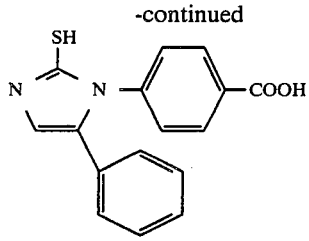

I-4

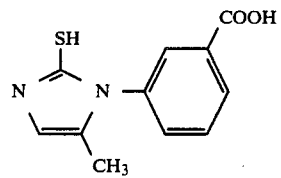

I-5

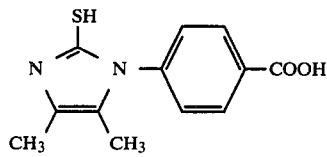

I-6

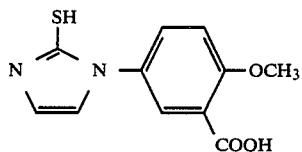

I-7

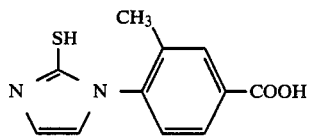

I-8

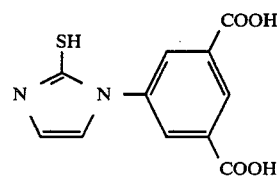

I-9

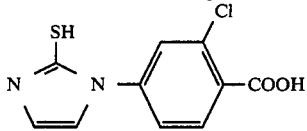

I-10

These compounds represented by general formula (I) can be synthesized in a conventional manner for synthesizing 2-mercaptoimidazoles and 2,3-dihydroimidazole-2-thiones. For example, they can be synthesized according to the processes described in U.S. Pat. Nos. 2,585,388, 2,541,924, Chemical Abstracts, 58, 7921g (1963), I.I. Kovtunovskaya Levshine, Tr. Ukr. Eksperim Endokrinol, Vol. 18, p. 345 (1961), M. Chamdon et al., Bull. Soc. Chim. Fr., 723 (1954), D. A. Shirley & D. W. Alley, J. Amer. Chem. Soc., 79, 4922 (1957), and A. Wohl. W. Marckwald, Ber., 22, p. 568 (1889).

In particular, the synthesis of Compound I-1 is described in the aforesaid Chemical Abstracts. An alternative general reaction sequence for synthesizing Compound I-1 from a p-aminobenzoic ester (for example, an ethyl ester) is as follows. A p-aminobenzoic ester is treated with carbon disulfide and triethylamine to synthesize a corresponding triethylammonium dithiocarbamate, then the product is reacted with ethyl chloroformate or methyl chloroformate, followed by heating to produce a corresponding isothiocyanate. Aminoacetaldehyde diethylacetal is added to this isothiocyanate, then the product is heated in the presence of an acid to simultaneously cause cyclization and hydrolysis of ester, thus producing Compound I-1.

Derivatives of Compound I-1 may be synthesized in the same manner as described above.

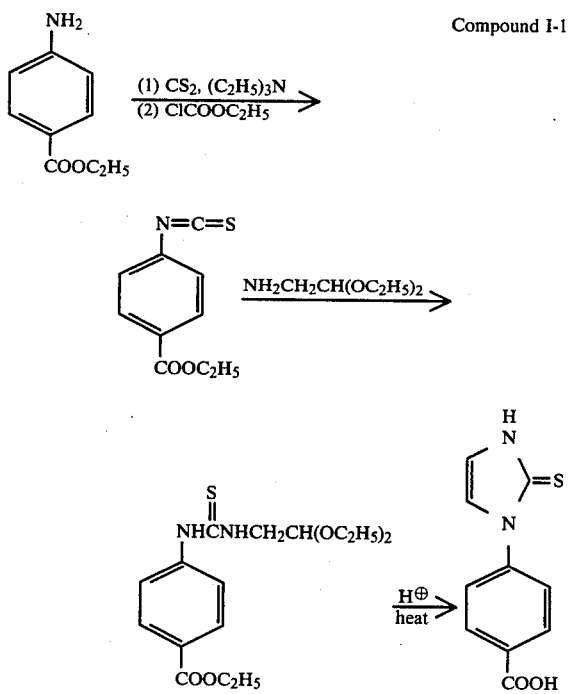

Compound I-1

The isothiocyanate used here (for example, p-carboethoxyphenyl isothiocyanate) may be synthesized according to the process described in, for example, S. R. Sandler and W. Karo, *Organic Functional Group Preparations*, pp. 312–315 (Academic Press, 1968).

A process for synthesizing the compounds represented by formula (I) of the present invention is described below by referring to specific synthesis examples. Compounds of the present invention not referred to in the synthesis examples may be synthesized according to the above-described known processes or according to the following synthesis examples.

In the following synthesis examples as well as examples described hereinafter, unless otherwise indicated, all percents are by weight.

SYNTHESIS EXAMPLE 1

Synthesis of Compound I-1

(1) Synthesis of N-(4-carboethoxyphenyl)-N'-(2,2-diethoxyethyl)thiourea 20 g of 4-carboethoxyphenyl isothiocyanate was dissolved in 50 ml of carbon tetrachloride, and 13 g of aminoacetaldehyde diethylacetal was dropwise added thereto in 5 minutes. Then, the resulting solution was stirred at room temperature for 1 hour. 50 ml of carbon tetrachloride was added to the reaction mixture, and crystals precipitated were collected by filtration, washed with 50 ml of carbon tetrachloride, then dried. Yield: 27.5 g (80.9 mol%).

(2) Synthesis of Compound I-1, [1-(4-carboxyphenyl)-2,3-dihydroimidazole-2-thione]

400 ml of 30% sulfuric acid was added to 80 g of N-(4-carboethoxyphenyl)-N'-(2,2-diethoxyethyl)thiourea, and the mixture was refluxed for 1 hour using an oil bath. The reaction mixture was cooled to room temperature, then 600 ml of water was added thereto, followed by cooling in an ice bath. Crystals precipitated were collected by filtration, then washed successively with 200 ml of water, 100 ml of isopropyl alcohol, and 100 ml of hexane. Yield: 48 g (92.8 mol%).

In compounds represented by general formula (II), as the atomic group represented by A, 5- or 7-membered hetero rings containing 1 to 4 nitrogen atoms are preferred. Specific examples thereof include imidazole, triazole and tetrazole. These atomic groups may be substituted by a lower alkyl group (e.g., a methyl group or an ethyl group).

The sulfo group-containing alkyl group represented by B includes, e.g., a sulfomethyl group, a sulfoethyl group and a sulfopropyl group. The alkyl group may be straight chained, branched chained or cyclic. The total number of carbon atoms in the alkyl group is preferably 1 to 14.

The sulfo group-containing aryl group represented by B includes, e.g., a sulfophenyl group and a sulfonaphthyl group. The total number of carbon atoms in the aryl group is preferably 6 to 14.

As the sulfo group-containing heterocyclic group represented by B, 5- to 7-membered hetero rings containing one or more of at least nitrogen, oxygen and sulfur, and substituted by a sulfo group are preferred. The hetero ring group includes, e.g., a pyridyl group and a furyl group.

The sulfo group in B is represented by $-SO_3M_1$ wherein $M_1$ is the same as defined for M. $M_1$ and M may be the same or different.

The number of sulfo groups in B is from 1 to 4, and is preferably 1 to 2.

These aryl, alkyl and hetero rings represented by B may have other substituents in addition to the sulfo group(s). Examples of such substituents include a halogen atom, a carboxyl group, an amino group, a cyano group, a nitro group, a sulfonyl group, a sulfamoyl group, a hetero ring, a carbamoyl group, an amido group, a hydroxyl group, a sulfonamido group and a ureido group.

Preferred specific examples of the compounds of the present invention represented by general formula (II) are illustrated below, which, however, are not to be construed as limiting the scope of the present invention in any way.

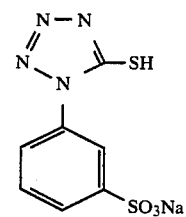

II-1

-continued
II-2
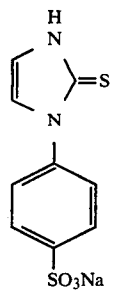
II-3
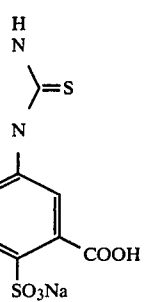
II-4
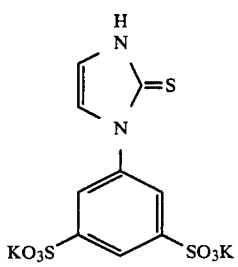
II-5
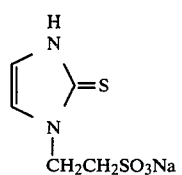
II-6
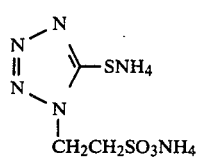
II-7
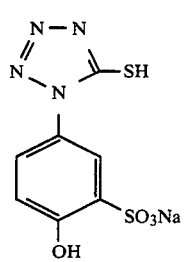
-continued
II-8
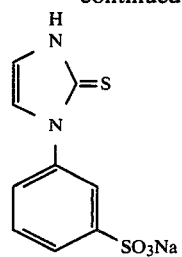
II-9
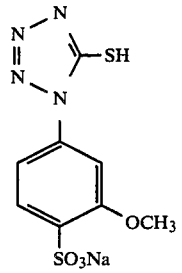
II-10
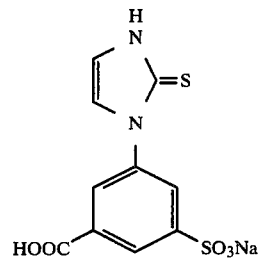
II-11
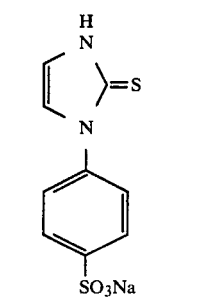
II-12
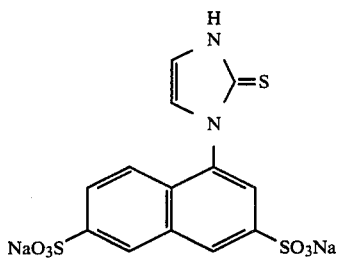
II-13
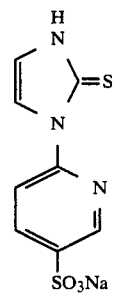

In general, heterocyclic thiourea compounds containing at least one sulfo group can be easily synthesized in a known manner using, as starting materials, isothiocyanates containing a sulfo group as a substituent.

The isothiocyanates containing a sulfo group may be synthesized according to the process described in British Pat. No. 1,275,701.

Examples of syntheses for specific compounds represented by general formula (II) of the present invention are described below. Other compounds of the present invention may be synthesized according to these examples. SYNTHESIS EXAMPLE 2

Synthesis of Compound II-1

(1) Synthesis of sodium 4-sulfophenylisothiocyanate 33.7 g of sulfanilic acid was suspended in 1,500 ml of water, and 7.8 g of sodium hydroxide was added thereto dropwise. After the reaction solution became uniform, 25 g of thiophosgene was slowly added dropwise thereto. After completion of the dropwise addition, the reaction was conducted for 1 hour at 40° C., followed by cooling the reaction solution to 5° C. Gradual addition of 380 g of NaCl into the above solution caused precipitation of crystals. The crystals formed were collected by filtration, washed successively with saturated NaCl aqueous sodium and ethanol/ether mixture, and dried. Yield: 47 g.

IR (nujol): 2,225, 2,175, 1,215 1,140, 1,050 cm$^{-1}$.

(2) 1-(4-Sulfophenyl)-5-mercaptotetrazole sodium salt 19.5 g of sodium azide was dissolved in 1.5 l of water, then 23.7 g of sodium 4-sulfophenylisothiocyanate synthesized in (1) above was added thereto. The resulting mixture was heated using a steam bath for 8 hours, followed by removing solids by filtration. After adding 125 ml of 20% sulfuric acid to the filtrate, it was concentrated under reduced pressure. Addition of 20 g of NaCl to the concentrate caused precipitation of crystals. The crystals were collected by filtration, then dissolved in a mixed solution of 80 ml of water and 20 ml of 2N HCl. Addition of NaCl thereto little by little caused precipitation of crystals. The crystals were collected by filtration and dried to obtain 7 g of Compound II-1.

IR (nujol): 1,225, 1,205, 1,142, 1,055, 1,048, 835, 761 cm$^{-1}$.

SYNTHESIS EXAMPLE 3

Synthesis of Compound II-2

23.7 g of sodium 4-sulfophenylisothiocyanate synthesized in Synthesis Example 2 was added to 500 ml of water, and stirred. 13.3 g of aminoacetaldehyde diethylacetal was added thereto, and the reaction was conducted at room temperature for 8 hours.

The reaction solution was then concentrated to 200 ml, acidified with sulfuric acid, and heated for 2 hours on a steam bath. After cooling, sodium chloride was added little by little thereto to saturation. Then, the solution was heated to 50° C. and a small amount of NaCl was further added thereto. Upon cooling the solution, crystals of Compound II-2 were precipitated. Yield: 6 g.

IR (nujol): 1,211, 1,175, 1,114, 903, 838 cm$^{-1}$.

SYNTHESIS EXAMPLE 4

Synthesis of Compound II-8

Sodium 3-sulfophenylisothiocyanate was synthesized in the same manner as sodium 4-sulfophenylisothiocyanate in Synthesis Example 2. 23.7 g of this sodium 3-sulfophenylisothiocyanate was suspended in 250 ml of water, 13.3 g of aminoacetaldehyde diethylacetal was added thereto, and the reaction was conducted at room temperature for 12 hours. 50 ml of concentrated HCl was added thereto and, after reacting for 4 hours on a steam bath, the solvent was distilled off under reduced pressure to concentrate the mixture to 150 ml. NaCl was added little by little at 50° to 60° C. and, when exceeding saturation, the solution was heated to completely dissolve the NaCl. Upon cooling to room temperature, Compound II-8 was precipitated as crystals. Recrystallization was conducted in the same manner as with Compound II-1. Yield 5 g.

IR (nujol): 1,195, 1,035, 801 cm$^{-1}$.

In compounds represented by general formula (III), the alkyl group represented by R preferably contains 1 to 8 carbon atoms (for example, a methyl group, an ethyl group, a propyl group, a hexyl group or an octyl group), and the aryl group preferably contains 6 to 10 carbon atoms (for example, a phenyl group or a naphthyl group).

Z represents an atomic group necessary for forming an optionally substituted, 5-membered hetero ring or an atomic group necessary for forming a 5-membered hetero ring fused with a benzene ring. As the 5-membered hetero ring, an imidazole ring, a triazole ring and a tetrazole ring are preferred and, as the substituent for the hetero ring, an alkyl group containing 1 to 8 carbon atoms (e.g., a methyl group, an ethyl group, a propyl group, a hexyl group or an octyl group) or an aryl group containing 6 to 10 carbon atoms (e.g., a phenyl group or a naphthyl group) is preferred. As the 5-membered hetero ring fused with a benzene ring, a benzimidazole group is preferred.

In compounds represented by general formula (III), at least one carbon atom must be substituted with a water-soluble group. The term "water-soluble group" as used herein means a group capable of making the compound water-soluble, and preferably includes a carboxyl group or its salt, a carbamoyl group (—CONH$_2$), a hydroxyl group, a sulfo group or its salt, an amino group (—NH$_2$) or a lower alkoxy group containing preferably 1 to 3 carbon atoms (e.g., a methoxy group, an ethoxy group or a propoxy group). Of these, a carboxyl group or its salt and a sulfo group or its salt are particularly preferred.

Of the compounds represented by general formula (III), those compounds represented by the following general formula (IIIa), (IIIb) or (IIIc) are particularly preferred.

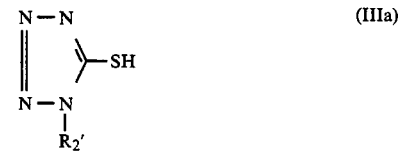

(IIIa)

In the above formula (IIIa), R$_2$' represents an alkyl group (containing preferably 1 to 8 carbon atoms) substituted with the above-described water-soluble group, or an aryl group (containing preferably 6 to 10 carbon atoms) substituted with the above-described water-soluble group. As the water-soluble group, a carboxyl group or its salt, a carbamoyl group, a hydroxyl group, a sulfo group or its salt, or an amino group are preferred, with a carboxyl group or its salt and a sulfo group or its salt being particularly preferred.

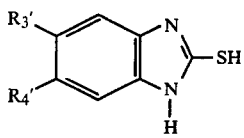

(IIIb)

In the above general formula (IIIb), $R_3'$ and $R_4'$, which may be the same or different, each represents a hydrogen atom, a halogen atom or the aforesaid water-soluble group, with the proviso that at least one of $R_3'$ and $R_4'$ is a water-soluble group. The water-soluble group includes a carboxyl group or its salt, a carbamoyl group, a hydroxyl group, a sulfo group or its salt, an amino group and a lower alkoxy group, with a carboxyl group or its salt and a sulfo group or its salt being particularly preferred.

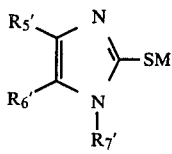

(IIIc)

In the above formula (IIIc), $R_5'$ and $R_6$, which may be the same or different, each represents a hydrogen atom, an alkyl group, an aryl group or a hetero ring group, $R_7'$ represents a phenyl group containing at least one carboxyl group, and M represents a hydrogen atom, NH$_4$ or an alkali metal (e.g., Na or K). The alkyl group represented by $R_5'$ or $R_6'$ may be substituted with a halogen atom (e.g., a chlorine atom or a bromine atom), an alkoxy group or a hydroxyl group, and includes a methyl group, an ethyl group, a methoxyethyl group, an ethoxyethyl group, a chloroethyl group and a benzyl group. The alkyl group preferably contains 1 to 14 carbon atoms.

The aryl group represented by $R_5'$ or $R_6'$ may be substituted with a halogen atom (e.g., a chlorine atom or a bromine atom), an alkyl group, an alkoxy group, an alkylsulfonyl group, an arylsulfonyl group, a sulfamoyl group, an alkylsulfonamido group, an arylsulfonamido group, a carbamoyl group or a carbonamido group. The aryl group preferably contains 6 to 14 carbon atoms.

As the hetero ring group represented by $R_5'$ or $R_6'$ substituted or unsubstituted, 5- to 7-membered hetero ring groups containing one or more of at least one kind of nitrogen, oxygen, and sulfur are preferred.

The number of carboxyl groups in the phenyl group represented by $R_7'$ is preferably 1 or 2.

The phenyl group represented by $R_7'$ may further be substituted with, e.g., a halogen atom (e.g., a chlorine atom or a bromine atom), an alkyl group (e.g., a methyl group or an ethyl group), an alkoxy group (e.g., a methoxy group or an ethoxy group), an alkylsulfonyl group, an arylsulfonyl group, a sulfamoyl group, an alkylsulfonamido group, an arylsulfonamido group, a carbamoyl group or a carbonamido group. These substituents preferably contain not more than 14 carbon atoms.

Of the compounds represented by general formulae (IIIa), (IIIb) and (IIIc), compounds represented by general formula (IIIc) are preferred.

Preferred specific examples of the compounds represented by general formula (III) are shown below, which, however, are not to be construed as limiting the scope of the present invention in any way.

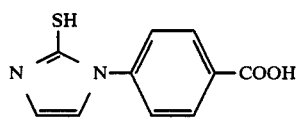

III-1

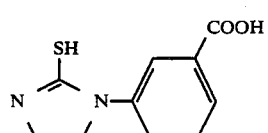

III-2

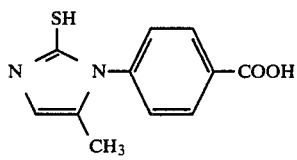

III-3

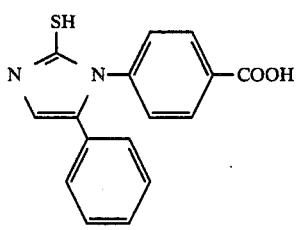

III-4

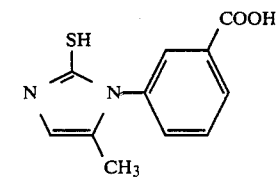

III-5

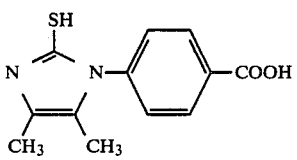

III-6

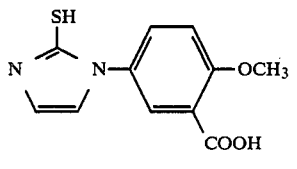

III-7

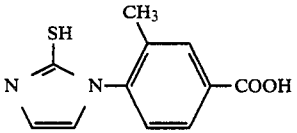

III-8

-continued
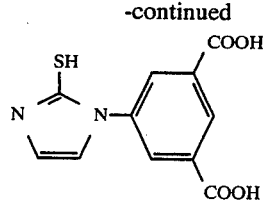 III-9
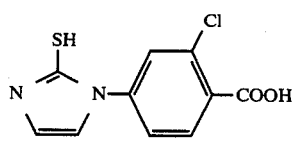 III-10
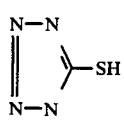 III-11
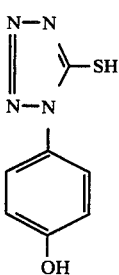 
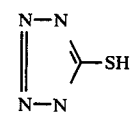 III-12
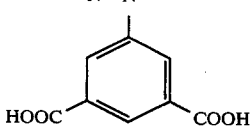 
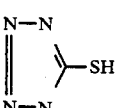 III-13
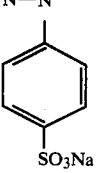 
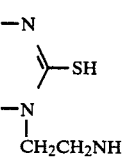 III-14
III-15
-continued
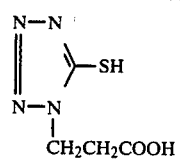 III-16
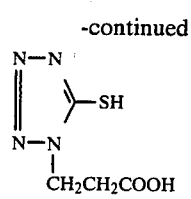 III-17
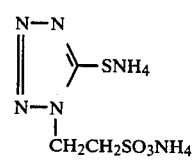 III-18
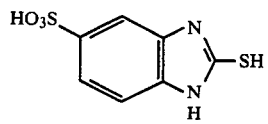 III-19
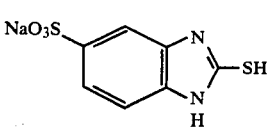 III-20
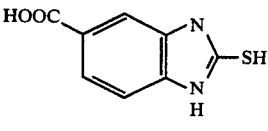 III-21
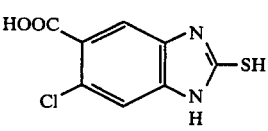 III-22
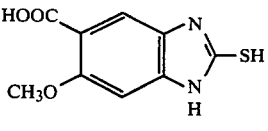 III-23
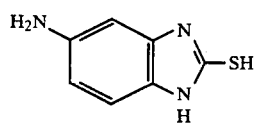 III-24
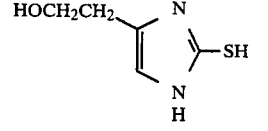 III-25
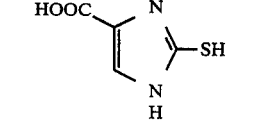 III-26

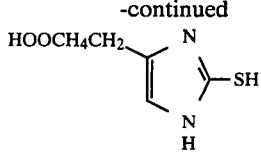 III-27

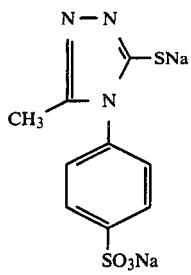 III-28

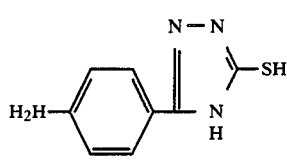 III-29

These compounds represented by general formula (III) are known and may be easily synthesized according to the processes described in, for example, U.S. Pat. Nos. 2,585,388, 2,541,924, Japanese Patent Publication No. 21842/67, Japanese Patent Application (OPI) No. 50169/78, British Pat. No. 1,275,701, D. A. Berges et al., *Journal of Heterocyclic Chemistry*, Vol. 15, p. 981 (1978), *The Chemistry of Heterocyclic Compounds*, "Imidazole and Derivatives", Part I, pp. 336–339, *Chemical Abstracts*, 58, 7921 (1963), p. 384 and E. Hoggarth, *Journal of Chemical Society*, pp. 1160–1167 (1949).

In compounds represented by general formula (IV), $R_{11}$ and $R_{12}$ may be the same or different, and each represents a hydrogen atom; an alkyl group containing 1 to 6 carbon atoms and optionally substituted with a hydroxyl group, a halogen atom or the like, such as a methyl group, an ethyl group, a butyl group, a hydroxyethyl group or a 2-chloroethyl group; an aryl group optionally substituted with an alkyl group, a hydroxyl group, a halogen atom or the like, such as a phenyl group, a 4-methylphenyl group, a 4-hydroxyphenyl group or a 3-chlorophenyl group; an alkoxycarbonyl group such as an ethoxycarbonyl group; provided that $R_{11}$ and $R_{12}$ may combine to form a 5- or 6-membered unsaturated ring, such as a trimethylene group or a tetramethylene group, or to form a benzene ring optionally substituted with an alkyl group (e.g., a methyl group or an ethyl group), an aryl group (e.g., a phenyl group), an alkoxy group (e.g., a methoxy group or an ethoxy group), a halogen atom (e.g., a chlorine atom or a bromine atom).

$R_{13}$ and $R_{14}$ may be the same or different and each represents an alkyl group containing 1 to 10 carbon atoms and optionally substituted with a hydroxyl group, an alkoxy group, a halogen atom or the like (for example, a methyl group, an ethyl group, a 4-chlorobutyl group, a methoxyethyl group or an n-decyl group); an aralkyl group optionally substituted with a halogen atom, an alkyl group or an alkoxy group (for example, a benzyl group, a phenethyl group, a p-chlorobenzyl group, an m-methylbenzyl group or a p-methoxybenzyl group); or an aryl group optionally substituted with a halogen atom, an alkyl group, an alkoxy group, a nitro group, an amino group, an acylamino group, a carboxyl group or an alkoxycarbonyl group (for example, a phenyl group, a naphthyl group, an o-chlorophenyl group, a p-methylphenyl group, a p-methoxyphenyl group, a p-nitrophenyl group, a p-methoxycarbonylphenyl group, a p-ethylaminophenyl group or an m-acetylaminophenyl group).

X represents a sulfur atom, an oxygen atom, a selenium atom or $>N-R_{14}$, wherein $R_{14}$ is the same as defined above.

Preferred specific examples of the compounds of the present invention represented by general formula (IV) are described below which, however, do not limit the present invention in any way.

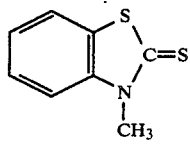 IV-1

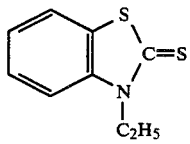 IV-2

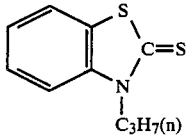 IV-3

 IV-4

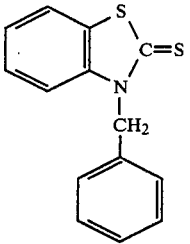 IV-5

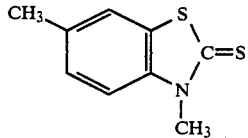 IV-6

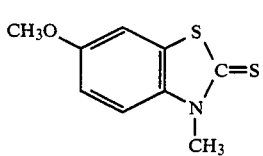 IV-7

-continued

IV-8: 6-chloro-3-methyl-benzothiazole-2-thione

IV-9: 3-(n-propyl)-5,6-dihydro-4H-cyclopenta[d]thiazole-2(3H)-thione

IV-10: 3-methyl-4,5,6,7-tetrahydrobenzothiazole-2(3H)-thione

IV-11: 3-(2-hydroxyethyl)-4-phenyl-thiazole-2(3H)-thione

IV-12: 3,4-dimethyl-thiazole-2(3H)-thione

IV-13: 3-phenyl-4-methyl-5-(ethoxycarbonyl)-thiazole-2(3H)-thione

IV-14: 4-methyl-3-(2-pyridyl)-thiazole-2(3H)-thione

IV-15: 4-methyl-3-(2-methylphenyl)-thiazole-2(3H)-thione

IV-16: 3-(4-methoxyphenyl)-4-phenyl-thiazole-2(3H)-thione

IV-17: 3-(4-chlorophenyl)-4-methyl-thiazole-2(3H)-thione

IV-18: 3-methyl-benzoxazole-2(3H)-thione

IV-19: 3-(n-propyl)-benzoxazole-2(3H)-thione

IV-20: 3-methyl-benzoselenazole-2(3H)-thione

IV-21: 1,3-dimethyl-benzimidazole-2(3H)-thione

IV-22: 1,3-di(n-propyl)-benzimidazole-2(3H)-thione

IV-23: 1,3-di(n-decyl)-benzimidazole-2(3H)-thione

-continued

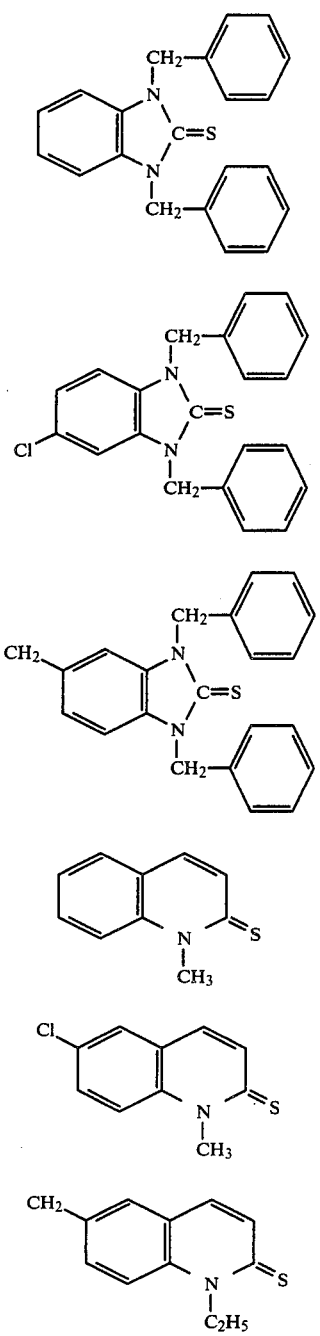

IV-24

IV-25

IV-26

IV-27

IV-28

IV-29

The compounds represented by general formula (IV) can be synthesized according to conventional, well known processes described in, for example, Japanese Patent Publication Nos. 34169/73 and 23368/74.

In the silver halide photographic light-sensitive material containing the compound represented by general formula (III), the deterioration of silver images with time can be prevented, however, the image-blackening cannot be prevented. The phenomenon of image-blackening caused by side exposure of a photographic light-sensitive material cannot be effectively prevented by adding benzotriazoles or tetrazoles both of which are well known as an image-blackening inhibitor, and in some cases, the addition of these inhibitors can cause more image-blackening. Incorporation of the compound represented by general formula (IV) with the compound represented by general formula (III) markedly depress the image-blackening phenomenon without deteriorating storage stability of silver images with time.

The stabilization of silver images can be attained by the use of the compound represented by general formula (I) or (II) or combination of the compound represented by general formula (III) and the compound represented by general formula (IV) in almost the same degree. The prevention of image-blackening can be attained by the use of the compound represented by general formula (I) or (II) or combination of the compound represented by general formula (III) and the compound represented by general formula (IV), and among them combination use of the compound of general formula (III) and the compound of general formula (IV) is particularly preferred.

The compound represented by general formula (I) or (II) or the combination of the compounds represented by general formulae (III) and (IV) is added to a silver halide emulsion layer or a layer adjacent to the emulsion layer. The compound is preferably added before coating the layer, but it is also possible, for example, to impregnate the layer with a solution of the compound after coating the layer.

The compound represented by general formula (I) or (II) is used in an amount of, preferably, about $1 \times 10^{-4}$ to $1 \times 10^{-2}$ mol, and particularly preferably about $2 \times 10^{-4}$ to $8 \times 10^{-3}$ mol, per mol of coated silver.

The combination of the compound represented by general formula (III) and the compound represented by general formula (IV) is used in an amount of, preferably about $2 \times 10^{-4}$ to $2 \times 10^{-2}$ mol, and particularly preferably about $4 \times 10^{-4}$ to $1.6 \times 10^{-2}$ mol in total, per mol of coated silver. The ratio of the compound represented by general formula (III) to that represented by general formula (IV) is in the range of about 1/100 to 100/1, preferably about 1/40 to 40/1 by weight.

The compound represented by general formula (III) and the compound represented by general formula (IV) are preferably both incorporated in the same emulsion layer. However, it is also possible to add one compound to a silver halide emulsion layer and the other to a layer adjacent to the silver halide emulsion layer.

In the present invention, the term "water-impermeable support" means any support which is completely impermeable to water or only extremely slightly permeable to water, which is opposite to "water-permeable support" such as a baryta paper support or a paper support without any coating. Examples of such supports include transparent plastic films such as cellulose triacetate and polyethylene terephthalate, whitened plastic films prepared by coating a white pigment such as titanium white dispersed in a binder (e.g., gelatin) on the above-described plastic films, and paper supports double-laminated with a hydrophobic polymer such as polyethylene.

The supports used in the present invention may, if desired, be subjected to conventional surface treatments such as chemical treatment, discharge treatment or UV-ray treatment, which may be replaced by, or combined with, application of a subbing layer.

The silver halide used in the silver halide light-sensitive material of the present invention includes silver chloride, silver chlorobromide, silver bromide, silver bromoiodide or silver chlorobromoiodide, and the particle size of the silver halide grains is not particularly limited, with a mean grain size of not more than about 4μ being preferred.

The silver halide emulsions may be primitive emulsions without chemical sensitization, but they are usually chemically sensitized. Chemical sensitization can be conducted according to the processes described in the aforesaid books by Glafkides or Zelikman et al. or in H. Frieser, *Die Gründlagen der Photographischen Prozesse mit Silberhalogeniden* (Akademische Verlagsgesellschaft, 1968).

Useful chemical sensitization methods include sulfur sensitization using thiosulfates, thioureas, thiazoles and rhodanines or active gelatin; reduction sensitization using stannous salts, amines, hydrazines, formamidinesulfinic acid and silane compounds; and noble metal sensitization using complexes of the group VIII metals such as iridium and palladium as well as gold metal complexes can be employed along or in combination.

The light-sensitive material of the present invention may contain a polyalkylene oxide or its ether, ester or amine derivative, a thioether compound, a thiomorpholine, a quaternary ammonium salt compound, a urethane derivative, a urea derivative, an imidazole derivative or a 3-pyrazolidone for the purpose of enhancing sensitivity or contrast or for accelerating development, including those described in U.S. Pat. Nos. 2,400,532, 2,423,549, 2,716,062, 3,617,280, 3,772,021 and 3,808,003.

As a binder or protective colloid for the photographic emulsion of the present invention, gelatin is advantageously used. However, other hydrophilic colloids can be used as well, including proteins such as gelatin derivatives, graft polymers between gelatin and other high polymers, albumin or casein; cellulose derivatives such as hydroxyethyl cellulose, carboxymethyl cellulose or cellulose eulfate; sugar derivatives such as sodium alginate and starch derivatives; and various synthetic hydrophilic substances such as homopolymers or copolymers (e.g., polyvinyl alcohol, partially acetalized polyvinyl alcohol, poly-N-vinyl pyrrolidone, polyacrylic acid, polymethacrylic acid, polyacrylamide, polyvinyl imidazole and polyvinyl pyrazole.

As a gelatin binder, acid-processed gelatin or enzyme-processed gelatin may be used, as well as lime-processed gelatin or a gelatin hydrolyzate or an enzyme-decomposed product.

The photographic light-sensitive material of the present invention may contain in its photographic emulsion layers or other hydrophilic colloidal layers various known surfactants for purposes such as improvement of coating properties, antistatic properties, slip properties, emulsion dispersibility, anti-adhesion properties, and photographic properties (for example, development acceleration, improvement of contrast and sensitization).

Useful surfactants include nonionic surfactants such as saponins, glycidol derivatives (e.g., alkenylsuccinic acid polyglycerides), fatty acid esters of polyhydric alcohols, sugar alkyl esters, urethanes and ethers; anionic surfactants such as triterpenoid saponins, alkylcarboxylic acid salts, alkylbenzenesulfonic acid salts, alkylsulfuric acid esters, alkylphosphoric acid esters, N-acyl-N-alkyltaurines, sulfosuccinic acid esters and sulfoalkylpolyoxyethylene alkylphenyl ethers; amphoteric surfactants such as amino acids, aminoalkylsulfonic acids, aminoalkylsulfuric or phosphoric esters, alkylbetaines, amineimides and amine oxides; and cationic surfactants such as alkylamine salts, aliphatic or aromatic quaternary ammonium salts, hetero ring quaternary ammonium salts such as pyridinium or imidazolium salts and aliphatic or hetero ring-containing phosphonium or sulfonium salts. However, it is not preferred to use polyalkylene oxide surface active agents in the present invention.

Photographic light-sensitive materials of the present invention may contain in the photographic emulsion layers or other hydrophilic colloidal layers a water-insoluble or slightly water-soluble synthetic polymer dispersion for the purpose of improving dimensional stability or the like. For example, polymers containing as monomer components alkyl (meth)acrylates, alkoxyalkyl (meth)acrylates, glycidyl (meth)acrylate, (meth)acrylamide, vinyl esters (e.g., vinyl acetate), acrylonitrile, olefin or styrene alone or in combination, or polymers containing as monomer components combinations of the above-described monomers and acrylic acid, methacrylic acid, α,β-unsaturated dicarboxylic acid, hydroxyalkyl (meth)acrylate, sulfoalkyl (meth)acrylate or styrenesulfonic acid may be used.

The photographic light-sensitive material of the present invention may contain an organic or inorganic hardener in its photographic emulsion layers or other hydrophilic colloidal layers. For example, chromium salts (e.g., chromium alum or chromium acetate), aldehydes (e.g., formaldehyde, glyoxal or glutaraldehyde), N-methylol compounds (e.g., dimethylolurea or methyloldimethylhydantoin), dioxane derivatives (e.g., 2,3-dihydroxydioxane), active vinyl compounds (e.g., 1,3,5-triacryloyl-hexahydro-s-triazine or bis(vinylsulfonyl)-methyl ether), active halogen compounds (e.g., 2,4-dichloro-6-hydroxy-s-triazine), mucohalogenic acids (e.g., mucochloric acid or mucophenoxychloric acid), isoxazoles, dialdehydo-starch and 2-chloro-6-hydroxytriazinylated gelatin can be used alone or in combination.

The photographic emulsion to be used in the present invention may be spectrally sensitized with methine dyes or the like, including cyanine dyes, merocyanine dyes, complex cyanine dyes, complex merocyanine dyes, holopolar cyanine dyes, hemicyanine dyes, styryl dyes and hemioxonol dyes. Particularly useful dyes are cyanine dyes, merocyanine dyes, and complex merocyanine dyes. In these dyes, any nuclei ordinarily used as basic hetero ring nuclei in cyanine dyes can be used, including a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus or a pyridine nucleus; those in which these nuclei are fused with an alicyclic hydrocarbon ring and those in which these nuclei are fused with an aromatic ring, e.g., an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus or a quinoline nucleus. These nuclei may be substituted at the nuclei carbon atoms.

In the merocyanine dyes or complex merocyanine dyes, 5- or 6-membered hetero ring nuclei such as a pyrazolin-5-one nucleus, a thiohydantoin nucleus, a 2-thiooxazolidine-2,4-dione nucleus, a thiazolidine-2,4-dione nucleus, a rhodanine nucleus or a thiobarbituric acid nucleus may be used as ketomethylene-containing nuclei.

The light-sensitive material of the present invention may contain in its hydrophilic layer a water-soluble dye (e.g., an oxonol dye, a hemioxonol dye, a styryl dye, a merocyanine dye, a cyanine dye or an azo dye) as a filter dye or for various purposes such as anti-irradiation.

The silver halide photographic light-sensitive material of the present invention contains as a mercapto anti-fogging agent only the compound represented by the foregoing general formula (I), but known non-mercapto anti-fogging agents or stabilizing agents may be used in combination with compound (I). Useful anti-fogging agents or stabilizing agents include benzothiazolium salts, nitroindazoles, nitrobenzimidazoles, chlorobenzimidazoles, bromobenzimidazoles, aminotriazoles, benzotriazoles, nitrobenzotriazoles, benzenethiosulfonic acids, benzenesulfinic acids, benzenesulfonic acid amides, azaindenes (e.g., triazaindenes, tetraazaindenes, and particularly, 4-hydroxy-substituted (1,3,3a,7)-tetraazaindenes).

In the present invention, any conventional exposure for obtaining photographic images may be used, including exposure by various light sources such as natural light (sunlight), a tungsten lamp, a fluorescent lamp, a mercury lamp, a xenon arc lamp, a carbon arc lamp, a xenon flash lamp or a cathode ray tube. As exposure time, an exposure time of 1/1,000 second to 1 second employed for ordinary cameras can be used as well as an exposure time shorter than 1/1,000 second, for example, $1/10^4$ to $1/10^6$ second using a xenon flash lamp or a cathode ray tube, and an exposure time longer than 1 second.

In photographic processing of the light-sensitive material of the present invention, any known developing processes for forming a silver image may be used, and any known processing solutions may be used. Processing temperature is usually between 18° and 50° C. However, temperatures lower than 18° C. or higher than 50° C. may be employed, if desired. Typical developing solutions for black-and-white photographic processing contain known developing agents, such as dihydroxybenzenes (e.g., hydroquinone), 3-pyrazolidones (e.g., 1-phenyl-3-pyrazolidone), aminophenols (e.g., N-methyl-p-aminophenol), 1-phenyl-3-pyrazolines, ascorbic acid, and hetero ring compounds (e.g., those having a 1,2,3,4-tetrahydroquinoline ring fused with an indolene nucleus described in U.S. Pat. No. 4,067,872), which can be used alone or in combination. Generally, the developing solution used contains known preservatives, alkali agents, pH buffers and anti-fogging agents, and if desired, may also contain dissolving aids, toning agents, development accelerators, surfactants, defoaming agents, water-softening agents, hardeners and viscosity-imparting agents.

Any conventional fixing solution can be used, containing as a fixing agent organic sulfur containing fixing agents as well as thiosulfates and thiocyanates. The fixing solution may contain a water-soluble aluminum salt as a hardener.

The use of the compound represented by general formula (I) or (II) or the combination of the compound represented by general formula (III) and the compound representd by general formula (IV) as an anti-fogging agent in the silver halide photographic light-sensitive material of the present invention offers the following advantages:

(1) even if a water-impermeable support is used, silver images simply formed by conventional black-and-white photographic processing have high stability and are free from deterioration with time;

(2) blackening of images by side exposure is reduced;

(3) fog is fully suppressed;

(4) thus, the silver halide photographic light-sensitive material of the present invention produces excellent microfilms or a black-and-white photographic printing paper.

The present invention will now be described in more detail by reference to the following examples, which are not to be construed as limiting the scope of the present invention. Unless otherwise indicated, all parts, ratios and percents are by weight.

EXAMPLE 1

To an acid-processed silver chlorobromide emulsion (silver bromide: 50 mol%) which had been prepared by precipitating grains by the double jet method, physically ripening and desalting the grains in a conventional manner, and sulfur-sensitizing, were added $1.2 \times 10^{-2}$ mol per mol of silver of 2,4-dichloro-6-hydroxy-1,3,5-triazine sodium salt (hardener) and $1.5 \times 10^{-3}$ mol per mol of silver of sodium dodecylbenzenesulfonate (coating aid). Then, one of the anti-fogging agents in Table 1 was added thereto in an amount of $1.7 \times 10^{-3}$ mol per mol of silver, and each of the resulting coating solutions was coated on a polyethylene-double-laminated paper support in a silver amount of 20 mg/dm$^2$ to prepared Samples 1 to 14.

Each of Samples 1 to 14 was subjected to the following measurements of photographic properties. Results are tabulated in Table 1.

(A) Measurement of Fogging Properties

Samples 1 to 14 were left for 3 days in a dark box at 50° C. and 80% RH, then developed at 30° C. for 1 minute without exposure using a developer, Fuji DP-Papinal C (made by Fuji Photo Film Co., Ltd.), stopped at room temperature for 30 seconds, fixed at room temperature for 5 minutes using Fuji Fix (made by Fuji Photo Film Co., Ltd.), washed with water at room temperature for 10 minutes and dried. Then, the fog density of each sample was measured.

(B) Measurement of Relative Sensitivity

Samples 1 to 14 were exposed through a continuous wedge using a sensitometer containing a tungsten lamp (1 second, 316 cms), then developed with the same developer as that used in (A) at 20° C. for 1 minute, stopped, fixed, washed with water and dried. Then, the relative sensitivity of each sample was measured.

(C) Measurement of Deterioration with Time of Silver Image

Samples 1 to 14 were exposed through a step wedge, then developed with the same developer as used in (A) at 32° C. for 24 seconds using an automatic developing machine, fixed at 32° C. for 30 seconds using Fuji Fix, washed with water at room temperature for 24 seconds, and dried. The thus-processed samples were left for 20 minutes in a nitrogen dioxide gas atmosphere (3,000 ppm) as described in British Patent Application (published unexamined) No. 2,019,024A, then exposed for 2 days outdoors (under sunlight). The degree of deterioration of silver image formed in image portion was observed and evaluated according to the following rating:

o: no deterioration of silver image;
Δ: silver image somewhat deteriorated (practically acceptable limit); and
X: serious deterioration of silver image.

(D) Blackening Degree of Image by Side Exposure

Samples 1 to 14 (two samples each) were identically exposed through a continuous wedge using a densitometer having a tungsten lamp. Then, one of each two samples was developed at 20° C. for 3 minutes using the same developer as used in (A) under a safelight fitted with a normal safelight filter, ND-2A (made by Fuji Photo Film Co., Ltd.), and the other was identically developed under a safelight fitted with a faded (color density-reduced) safelight filter, ND-2A, then fixed. The samples were washed with water and dried. The sensitivities were determined by the exposure required to give an optical density of 1.0, and the difference between the density obtained by using a normal safelight filter and that obtained by using a faded safelight filter, Δ log E, was determined for each sample. Results are given in Table 1.

TABLE 1

| Sample No. | Added Compound | Photographic Properties | | | | Remarks |
|---|---|---|---|---|---|---|
| | | Relative Sensitivity | Fog | Stability of Silver Image | Degree of Image-Blackening by Side Exposure | |
| 1 | — | 100 | 0.14 | o | 0.15 | Comparison |
| 2 | a | 75 | 0.14 | x | 0.07 | Comparison |
| 3 | b | 50 | 0.00 | o | 0.13 | Comparison |
| 4 | c | 57 | 0.00 | o | 0.20 | Comparison |
| 5 | d | 80 | 0.00 | Δ | 0.13 | Comparison |
| 6 | I-1 | 73 | 0.00 | o | 0.06 | Invention |
| 7 | I-9 | 77 | 0.00 | o | 0.06 | Invention |
| 8 | I-3 | 75 | 0.00 | o | 0.07 | Invention |
| 9 | I-5 | 80 | 0.00 | o | 0.07 | Invention |
| 10 | I-10 | 73 | 0.00 | o | 0.06 | Invention |
| 11 | II-1 | 80 | 0.00 | o | 0.11 | Invention |
| 12 | II-2 | 81 | 0.00 | o | 0.07 | Invention |
| 13 | II-7 | 75 | 0.00 | o | 0.11 | Invention |
| 14 | II-8 | 69 | 0.00 | o | 0.08 | Invention |

Compounds a, b, c and d are as follows:

Compound a

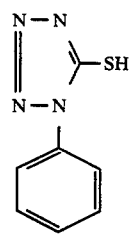

(described in Japanese Patent Application (OPI) No. 14836/82)

Compound b

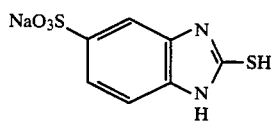

(described in Japanese Patent Application (OPI) No. 14836/82)

Compound c

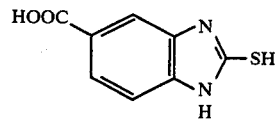

(described in Japanese Patent Application (OPI) No. 14836/82)

Compound d

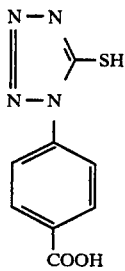

(described in Japanese Patent Application (OPI) No. 14836/82)

As is clear from Table 1, Samples 6 to 14 using the compounds of the present invention showed less reduction in sensitivity, better silver image stability, and markedly reduced blackening by side exposure than Comparative Samples 2 to 5.

Additionally, the comparative samples show such significant blackening resulting from side exposure that their practical use is questionable.

EXAMPLE 2

To an acid-processed silver chlorobromide emulsion (silver bromide: 50 mol%) which had been prepared by precipitating grains by the double jet method, physically ripening and desalting the grains in a conventional manner, and sulfur-sensitizing, were added $1.2 \times 10^{-2}$ mol per mol of silver of 2,4-dichloro-6-hydroxy-1,3,5-triazine sodium salt (hardener) and $1.5 \times 10^{-3}$ mol per mol of silver of sodium dodecylbenzenesulfonate (coating acid). Then, one of the anti-fogging agents given in Table 2 was added thereto in an amount described in Table 2, and each of the resulting coating solutions was coated on a polyethylene-double-laminated paper support in a silver amount of 16 mg/dm² to prepare Samples 15 to 44.

Each of these Samples 15 to 44 was subjected to the same measurements as described in Example 1. Results thus obtained are tabulated in Table 2.

pound represented by general formula (III), can be markedly depressed by the addition of the compound represented by general formula (IV) without seriously reducing relative sensitivity. In addition, silver images stable after photographic processing were obtained

TABLE 2

| Sample No. | Added Compound (mol/mol Ag) | Relative Sensitivity | Fog | Stability of Silver Image | Degree of Image-Blackening by Side Exposure | Remarks |
|---|---|---|---|---|---|---|
| 15 | Compound a ($1.7 \times 10^{-3}$) | 130 | 0.00 | x | 0.04 | Comparison |
| 16 | III-1 ($1.7 \times 10^{-3}$) | 146 | 0.00 | o | 0.06 | " |
| 17 | III-1 ($1.7 \times 10^{-3}$) + Compound e ($2 \times 10^{-3}$) | 140 | 0.00 | o | 0.08 | " |
| 18 | III-1 ($1.7 \times 10^{-3}$) + Compound f ($2 \times 10^{-3}$) | 146 | 0.00 | o | 0.18 | " |
| 19 | III-1 ($1.7 \times 10^{-3}$) + Compound g ($2 \times 10^{-3}$) | 146 | 0.00 | o | 0.15 | " |
| 20 | III-1 ($1.7 \times 10^{-3}$) + IV-1 ($2 \times 10^{-3}$) | 146 | 0.00 | o | 0.03 | Invention |
| 21 | III-1 ($1.7 \times 10^{-3}$) + IV-12 ($2 \times 10^{-3}$) | 130 | 0.00 | o | 0.03 | " |
| 22 | III-1 ($1.7 \times 10^{-3}$) + IV-18 ($2 \times 10^{-3}$) | 135 | 0.00 | o | 0.04 | " |
| 23 | III-1 ($1.7 \times 10^{-3}$) + IV-21 ($2 \times 10^{-3}$) | 130 | 0.00 | o | 0.04 | " |
| 24 | III-3 ($1.7 \times 10^{-3}$) | 140 | 0.00 | o | 0.08 | Comparison |
| 25 | III-3 ($1.7 \times 10^{-3}$) + IV-2 ($2 \times 10^{-3}$) | 140 | 0.00 | o | 0.04 | Invention |
| 26 | III-3 ($1.7 \times 10^{-3}$) + IV-7 ($2 \times 10^{-3}$) | 140 | 0.00 | o | 0.05 | " |
| 27 | III-3 ($1.7 \times 10^{-3}$) + IV-12 ($2 \times 10^{-3}$) | 120 | 0.01 | o | 0.05 | " |
| 28 | III-9 ($1.7 \times 10^{-3}$) | 150 | 0.00 | o | 0.07 | Comparison |
| 29 | III-9 ($1.7 \times 10^{-3}$) + IV-1 ($2 \times 10^{-3}$) | 150 | 0.00 | o | 0.03 | Invention |
| 30 | III-9 ($1.7 \times 10^{-3}$) + IV-7 ($2 \times 10^{-3}$) | 150 | 0.00 | o | 0.04 | Invention |
| 31 | III-9 ($1.7 \times 10^{-3}$) + IV-12 ($2 \times 10^{-3}$) | 140 | 0.01 | o | 0.03 | " |
| 32 | III-9 ($1.7 \times 10^{-3}$) + IV-21 ($2 \times 10^{-3}$) | 140 | 0.00 | o | 0.05 | " |
| 33 | III-11 ($1.7 \times 10^{-3}$) | 130 | 0.00 | Δ | 0.13 | Comparison |
| 34 | III-11 ($1.7 \times 10^{-3}$) + IV-1 ($2 \times 10^{-3}$) | 130 | 0.00 | Δ | 0.08 | Invention |
| 35 | III-19 ($1.7 \times 10^{-3}$) | 100 | 0.00 | o | 0.13 | Comparison |
| 36 | III-19 ($1.7 \times 10^{-3}$) + IV-1 ($2 \times 10^{-3}$) | 100 | 0.00 | o | 0.08 | Invention |
| 37 | III-19 ($1.7 \times 10^{-3}$) + IV-12 ($2 \times 10^{-3}$) | 90 | 0.00 | o | 0.08 | " |
| 38 | III-20 ($1.7 \times 10^{-3}$) | 130 | 0.00 | o | 0.13 | Comparison |
| 39 | III-20 ($1.7 \times 10^{-3}$) + IV-1 ($2 \times 10^{-3}$) | 130 | 0.00 | o | 0.08 | Invention |
| 40 | III-20 ($1.7 \times 10^{-3}$) + IV-12 ($2 \times 10^{-3}$) | 115 | 0.00 | o | 0.08 | " |
| 41 | III-21 ($1.7 \times 10^{-3}$) | 120 | 0.01 | o | 0.12 | Comparison |
| 42 | III-21 ($1.7 \times 10^{-3}$) + IV-1 ($2 \times 10^{-3}$) | 120 | 0.00 | o | 0.07 | Invention |
| 43 | III-21 ($1.7 \times 10^{-3}$) + IV-7 ($2 \times 10^{-3}$) | 120 | 0.00 | o | 0.07 | " |
| 44 | III-21 ($1.7 \times 10^{-3}$) + IV-12 ($2 \times 10^{-3}$) | 110 | 0.01 | o | 0.07 | " |

Compounds e, f and g are as follows:

Compound e

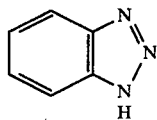

Compound f

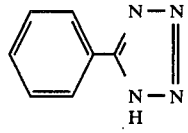

Compound g

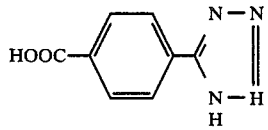

Compound a

Compound a is the same as that described in Example 1.

As is shown in Table 2, image-blackening by side exposure, which is caused by the addition of the com- (Sample Nos. 20 to 23, 25 to 27, 29 to 32, 34, 36, 37, 39, 40, and 42 to 44).

On the other hand, Sample Nos. 17 to 19 using Compounds e to g, respectively, showed greater image-blackening, and were not practically usable as photographic light-sensitive materials.

EXAMPLE 3

To a silver bromoiodide emulsion (silver bromide: 99 mol%), prepared by precipitating grains according to the double jet process, physically ripening in a conventional manner, sulfur-sensitizing, and gold-sensitizing, were added $1.2 \times 10^{-2}$ mol per mol of silver of 2,4-dichloro-6-hydroxy-1,3,5-triazine sodium salt (hardener) and $1.5 \times 10^{-3}$ mol per mol of silver of sodium dodecylbenzenesulfonate (coating aid). Then, $2 \times 10^{-3}$ mol per mol of silver of Compound III-9 and $2 \times 10^{-3}$ mol per mol of silver of Compound IV-1 were added thereto, and the resulting coating solution was coated on a support in a coated silver amount of 20 mg/dm² to prepare a sample.

When the thus-obtained sample was processed and evaluated in the same manner as in Example 1, the resulting silver image was stable, and image-blackening by side exposure was remarkably depressed by the addition of Compound IV-1.

While the invention has been described in detail and with reference to specific embodiments thereof, it will be apparent to one skilled in the art that various changes and modifications can be made therein without departing from the spirit and scope thereof.

What is claimed is:

1. A silver halide photographic light-sensitive material for obtaining a silver image comprising a water-impermeable support having at least one silver halide emulsion layer, and containing in association with said emulsion layer a compound selected from the group consisting of:
(a) a compound represented by the following general formula (I):

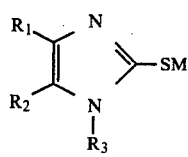
(I)

wherein $R_1$ and $R_2$, which may be the same or different, each represents a hydrogen atom, an alkyl group, an aryl group or a hetero ring group, $R_3$ represents a phenyl group containing at least one carboxyl group, and M represents a hydrogen atom, $NH_4$ or an alkali metal atom;
(b) a compound represented by the following general formula (II):

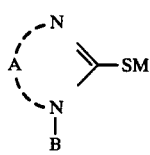
(II)

wherein A represents an atomic group necessary for forming an imidazole ring, B represents an aryl or a hetero ring group each substituted with at least one sulfo group, and M represents a hydrogen atom, $NH_4$ or an alkali metal atom; and
(c) a combination of a compound represented by the following general formula (III) and a compound represented by the following general formula (IV):

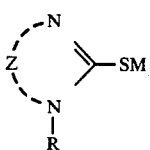
(III)

wherein M represents a hydrogen atom, $NH_4$ or an alkali metal atom, R represents a hydrogen atom, an alkyl group or an aryl group, and Z represents an atomic group necessary for forming an optionally substituted, 5-membered hetero ring or an atomic group necessary for forming a 5-membered hetero ring fused with a benzene ring; and

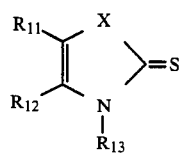
(IV)

wherein X is selected form the group consisting of a sulfur atom, an oxygen atom, a selenium atom, $>N-R_{14}$, wherein $R_{14}$ represents an alkyl group, an aralkyl group or an aryl group, and $-CH=$ $CH-$, $R_{11}$ and $R_{12}$, which may be the same or different, each represents a hydrogen atom, an alkyl group, an aryl group or an alkoxycarbonyl group, provided that $R_{11}$ and $R_{12}$ may combine to form a 5- or 6-membered ring, and $R_{13}$ represents an alkyl group, an aralkyl group or an aryl group.

2. The light-sensitive material claimed in claim 1, wherein said compound of general formula (III) is selected from the group consisting of compounds represented by the following general formulae (IIIa), (IIIb) and (IIIc):

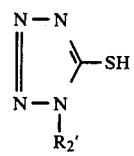
(IIIa)

wherein $R_2'$ represents an alkyl or an aryl group each substituted with a water-soluble group selected from the group consisting of a carboxyl group or its salt, a carbamoyl group, a hydroxyl group, a sulfo group or its salt, and an amino group;

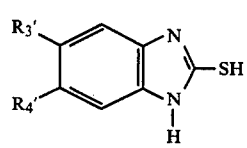
(IIIb)

wherein $R_3'$ and $R_4'$, which may be the same or different, each represents a hydrogen atom, a halogen atom, or a water-soluble group selected from the group consisting of a carboxyl group or its salt, a carbamoyl group, a hydroxyl group, a sulfo group or its salt, an amino group and a lower alkoxy group, provided that at least one of $R_3$ and $R_4$ is such a water-soluble group; and

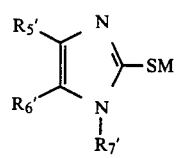
(IIIc)

wherein $R_5'$ and $R_6'$, which may be the same or different, each represents a hydrogen atom, an alkyl group, an aryl group, or a hetero ring group, $R_7'$ represents a phenyl group containing at least one carboxyl group, and M represents a hydrogen atom, $NH_4$ or an alkali metal atom.

3. The light-sensitive material claimed in claim 1, wherein said compound represented by general formula (I) or (II) is present in an amount of from about $1 \times 10^{-4}$ to $1 \times 10^{-2}$ mol per mol of silver.

4. The light-sensitive material claimed in claim 3, wherein said compound represented by general formula (I) or (II) is present in an amount of from about $2 \times 10^{-4}$ to $8 \times 10^{-3}$ mol per mol of silver.

5. The light-sensitive material claimed in claim 1, wherein the total amount of said compounds represented by general formulae (III) and (IV) present is from about $2 \times 10^{-4}$ to $2 \times 10^{-2}$ mol per mol of silver.

6. The light-sensitive material claimed in claim 5, wherein the total amount of said compounds represented by general formulae (III) and (IV) is from about $4 \times 10^{-4}$ to $1.6 \times 10^{-2}$ mol per mol of silver.

7. The light-sensitive material claimed in claim 5, wherein the mol ratio of said compound represented by general formula (III) of the compound represented by general formula (IV) is in the range of from about 1:100 to 100:1.

8. The light-sensitive material claimed in claim 7, wherein the mol ratio of said compound represented by formula (III) to said compound represented by formula (IV) is in the range of from about 1:40 to 40:1.

9. The light-sensitive material claimed in claim 1, wherein said compound represented by general formula (I) or (II) is present in said silver halide emulsion layer.

10. The light-sensitive material claimed in claim 1, wherein said compound of general formula (I) or (II) is present in a layer adjacent to said silver halide emulsion layer.

11. The light-sensitive material claimed in claim 1, wherein said compound represented by general formula (III) and said compound represented by general formula (IV) are present in said silver halide emulsion layer.

12. The light-sensitive material claimed in claim 1, wherein said compound represented by general formula (III) is present in said silver halide emulsion layer, and said compound represented by general formula (IV) is present in a layer adjacent to said silver halide emulsion layer.

13. The light-sensitive material claimed in claim 1, wherein said compound represented by general formula (IV) is present in said silver halide emulsion layer, and said compound represented by general formula (III) is present in a layer adjacent to said silver halide emulsion layer.

14. A method of forming silver images which comprises develping an exposed silver halide photographic light-sensitive material and thereafter fixing and water washing, wherein the silver halide photographic light-sensitive material comprises a water-impermeable support having at least one silver halide emulsion layer, and containing in association with said emulsion layer a compound selected from the group consisting of:

(a) a compound represented by the following general formula (I):

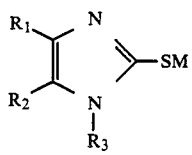

wherein $R_1$ and $R_2$, which may be the same or different, each represents a hydrogen atom, an alkyl group, an aryl group or a hetero ring group, $R_3$ represents a phenyl group containing at least one carboxyl group, and M represents a hydrogen atom, $NH_4$ or an alkali metal atom;

(b) a compound represented by the following general formula (II):

wherein A represents an atomic group necessary for forming an imidazole ring, B represents an aryl or a hetero ring group each substituted with at least one sulfo group, and M represents a hydrogen atom, $NH_4$ or an alkali metal atom; and (c) a combination of a compound represented by the following general formula (III) and a compound represented by the following general formula (IV):

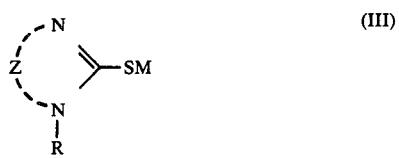

wherein M represents a hydrogen atom, $NH_4$ or an alkali metal atom, R represents a hydrogen atom, an alkyl group or an aryl group, and Z represents an atomic group necessary for forming an optionally substituted, 5-membered hetero ring or an atomic group necessary for forming a 5-membered hetero ring fused with a benzene ring; and

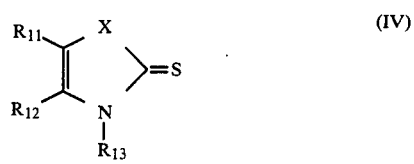

wherein X is selected form the group consisting of a sulfur atom, an oxygen atom, a selenium atom, $>N-R_{14}$, wherein $R_{14}$ represents an alkyl group, an aralkyl group or an aryl group, and $-CH=CH-$, $R_{11}$ and $R_{12}$, which may be the same or different, each represents a hydrogen atom, an alkyl group, an aryl group or an alkoxycarbonyl group, provided that $R_{11}$ and $R_{12}$ may combine to form a 5- or 6-membered ring, and $R_{13}$ represents an alkyl group, an aralkyl group or an aryl group.

15. The method of forming silver images claimed in claim 14, wherein said compound of general formula (III) is selected from the group consisting of compounds represented by the following general formulae (IIIa), (IIIb) and (IIIc):

wherein $R_2'$ represents an alkyl or an aryl group each substituted with a water-soluble group selected from the group consisting of a carboxyl group or its salt, a carbamoyl group, a hydroxyl group, a sulfo group or its salt, and an amino group;

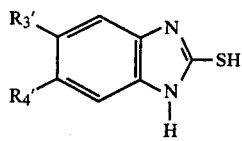
(IIIb)

wherein $R_3'$ and $R_4'$, which may be the same or different, each represents a hydrogen atom, a halogen atom, or a water-soluble group selected from the group consisting of a carboxyl group or its salt, a carbamoyl group, a hydroxyl group, a sulfo group or its salt, an amino group and a lower alkoxy group, provided that at least one of $R_3'$ and $R_4'$ is such a water-soluble group; and

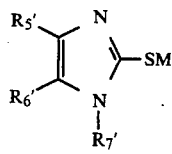
(IIIc)

wherein $R_5'$ and $R_6'$, which may be the same or different, each represents a hydrogen atom, an alkyl group, an aryl group, or a hetero ring group, $R_7'$ represents a phenyl group containing at least one carboxyl group, and M represents a hydrogen atom, $NH_4$ or an alkali metal atom.

16. The method of forming silver images claimed in claim 14, wherein said compound represented by general formula (I) or (II) is present in an amount of from about $1 \times 10^{-4}$ to $1 \times 10^{-2}$ mol per mol of silver.

17. The method of forming silver images claimed in claim 14, wherein the total amount of said compounds represented by general formulae (III) and (IV) present is from about $2 \times 10^{-4}$ to $2 \times 10^{-2}$ mol per mol of silver.

18. The method of forming silver images claimed in claim 14, wherein the mol ratio of said compound represented by general formula (III) to the compound represented by general formula (IV) is in the range of from about 1:100 to 100:1.

19. A silver halide photographic light-sensitive material for obtaining a silver image comprising a water-impermeable support having at least one silver halide emulsion layer, and containing in association with said emulsion layer a compound represented by the following general formula (I):

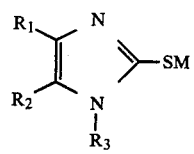
(I)

wherein $R_1$ and $R_2$, which may be the same or different, each represents a hydrogen atom, an alkyl group, an aryl group or a hetero ring group, $R_3$ represents a phenyl group containing at least one carboxyl group, and M represents a hydrogen atom, $NH_4$ or an alkali metal atom.

20. A silver halide photographic light-sensitive material for obtaining a silver image comprising a water-impermeable support having at least one silver halide emulsion layer, and containing in association with said emulsion layer a combination of a compound represented by the following general formula (III) and a compound represented by the following general formula (IV):

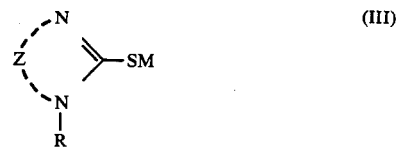
(III)

wherein M represents a hydrogen atom, $NH_4$ or an alkali metal atom, R represents a hydrogen atom, an alkyl group or an aryl group, and Z represents an atomic group necessary for forming an optionally substituted, 5-membered hetero ring or an atomic group necessary for forming a 5-membered hetero ring fused with a benzene ring; and

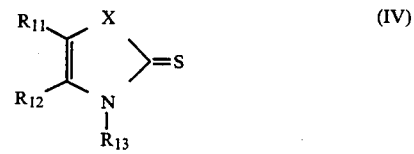
(IV)

wherein X is selected form the group consisting of a sulfur atom, an oxygen atom, a selenium atom, $>N-R_{14}$, wherein $R_{14}$ represents an alkyl group, an aralkyl group or an aryl group, and $-CH=CH-$, $R_{11}$ and $R_{12}$, which may be the same or different, each represents a hydrogen atom, an alkyl group, an aryl group or an alkoxycarbonyl group, provided that $R_{11}$ and $R_{12}$ may combine to form a 5- or 6-membered ring, and $R_{13}$ represents an alkyl group, an aralkyl group or an aryl group.

21. The light-sensitive material claimed in claim 1, wherein said emulsion layer contains a compound selected from the group consisting of: (a) a compound represented by general formula (I) or (c) a combination of a compound represented by the general formula (III) and a compound represented by the general formula (IV).

22. The method of forming silver images claimed in claim 14, wherein said emulsion layer contains a compound represented by general formula (I).

23. The method of forming silver images claimed in claim 14, wherein said emulsion layer contains a combination of a compound represented by the general formula (III) and a compound represented by the general formula (IV).

* * * * *